US007767220B2

(12) United States Patent
Ranade et al.

(10) Patent No.: US 7,767,220 B2
(45) Date of Patent: Aug. 3, 2010

(54) IMPLANTABLE OR INSERTABLE MEDICAL ARTICLES HAVING COVALENTLY MODIFIED, BIOCOMPATIBLE SURFACES

(75) Inventors: Shrirang V. Ranade, Arlington, MA (US); Michael N. Helmus, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1867 days.

(21) Appl. No.: 10/830,772

(22) Filed: Apr. 23, 2004

(65) Prior Publication Data
US 2005/0238684 A1 Oct. 27, 2005

(51) Int. Cl.
 *A61F 2/02* (2006.01)
 *A61F 2/00* (2006.01)
 *A61K 47/00* (2006.01)
(52) U.S. Cl. .................. 424/423; 514/772.1; 623/11.11; 623/1.46; 604/890.1; 604/891.1; 528/4; 528/9; 528/35
(58) Field of Classification Search ........................ None
 See application file for complete search history.

(56) References Cited

U.S. PATENT DOCUMENTS

| 5,289,831 | A | * | 3/1994 | Bosley | 128/899 |
|---|---|---|---|---|---|
| 5,567,495 | A | * | 10/1996 | Modak et al. | 428/36.9 |
| 5,733,925 | A | | 3/1998 | Kunz et al. | 514/449 |
| 5,849,368 | A | | 12/1998 | Hostettler et al. | 427/536 |
| 5,977,252 | A | | 11/1999 | Wagner et al. | 525/54.1 |
| 6,358,557 | B1 | * | 3/2002 | Wang et al. | 427/2.24 |
| 6,545,097 | B2 | | 4/2003 | Pinchuk et al. | 525/240 |
| 7,279,174 | B2 | * | 10/2007 | Pacetti et al. | 424/422 |
| 2001/0007083 | A1 | | 7/2001 | Roorda | 623/1.15 |
| 2002/0032414 | A1 | | 3/2002 | Ragheb et al. | 604/265 |
| 2002/0094440 | A1 | | 7/2002 | Llanos et al. | 428/421 |
| 2002/0107330 | A1 | | 8/2002 | Pinchuk et al. | 525/242 |
| 2002/0139975 | A1 | | 10/2002 | Lewis et al. | 257/40 |
| 2002/0171082 | A1 | | 11/2002 | Lewis | 257/56 |
| 2003/0175750 | A1 | | 9/2003 | Barany et al. | 435/6 |
| 2003/0235602 | A1 | | 12/2003 | Schwarz | 424/424 |
| 2005/0106203 | A1 | * | 5/2005 | Roorda et al. | 424/423 |
| 2006/0194008 | A1 | * | 8/2006 | Schwartz et al. | 428/34.4 |

FOREIGN PATENT DOCUMENTS

EP 0 567 285 A1 10/1993
WO WO 99/52574 10/1999
WO WO 03008110 A1 * 1/2003

OTHER PUBLICATIONS

Sheu, Min-Shyan, Hudson, David M., Loh, Ih-Houng, "Biomaterials Surface Modification Using Plasma Gas Discharge Processes." Encyclopedic Handbook of Biomaterials and Bioengineering, Part A Materials pp. 865-894, 1995.*
Fettes, E.M. (editor). "Chemical Reactions of Polymers". Interscience Publishers. pp. 1036-1040. 1964.
Ranade, Shrirang V., Xie, Xiang-Qun, DiBenedetto, Anthony T. "Effect of Interphase Structure on the Debonding of Polycarbonate from S-2 Glass Fibers". J. Adhesion. vol. 64. pp. 7-30. 1997.
Xie, X.-Q., Ranade, S.V., DiBenedetto, A. T. "A solid state NMR study of polycarbonate oligomer grafted onto the surface of amorphous silica". Polymer. vol. 40. pp. 6297-6306. 1999.
Dardik, H., et al., "Morphologic and Biophysical Assessment of Long Term Umbilical Cord Vein Implants Used As Vascular Conduits", *Surgery Gynecology and Obstetrics*, vol. 154, No. 1, 1982, pp. 17-26.
Baier, R.E., Meenaghan, M.A., Hartman, L.C., Wirth, J.E., Flynn, H.E., Meyer, A.E., Natiella, J.R., Carter, J.M., "Implant Surface Characteristics and Tissue Interaction", Journal Oral Implantol, vol. 13 i4, pp. 594-606, 1988.
Baier, R., Natiella, J., Meyer, A.,Carter, J., "Importance of Implant Surface Preparation for Biomaterials with Different Intrinsic Properties". Tissue Integration in Oral and Maxillo-Facial Reconstruction. 1986. pp. 13-41.
Baier, R., Natiella, J., Meyer, A.,Carter, J., Fornalik, M.S., Turnbull, T., "Surface Phenomena in In Vivo Environments". NATO Advanced Study Institute on Applications of Materials Sciences to the Practice of Implant Orthopedic Surgery. Marbella, Spain. pp. 153-188. 1984.

(Continued)

*Primary Examiner*—S. Tran
*Assistant Examiner*—Caralynne Helm
(74) *Attorney, Agent, or Firm*—Mayer & Williams PC; David B. Bonham; Keum J. Park

(57) ABSTRACT

Implantable or insertable medical devices comprising a surface region that is modified by covalently coupling a molecular species (or a combination of molecular species) to the same. The molecular species are selected such that the resulting modified surface region has critical surface energy between 20 and 30 dynes/cm. In certain embodiments, the covalently coupled molecular species comprise one or more methyl groups. An advantage of the present invention is that novel medical devices are provided, which have a surface with a critical surface energy value that has been shown to display enhanced biocompatibility, including enhanced thromboresistance, relative to other surfaces.

15 Claims, No Drawings

OTHER PUBLICATIONS

Baier, R., Natiella, J., Natiella, R., Meyer, A., Carter, J., "Surface properties determine bioadhesive outcomes: methods and results", Journal Biomed Mater Research. vol. 18 i4. pp. 337-355. 1984.

Natiella, J., Baier, R., Carter, J., Meyer, A., Meenaghan, M.A., Flynn, H.E., "Differences in Host Tissue Reactions to Surface-Modified Dental Implants". 785th ACS National Meeting. American Chemical Society. 1983.

Zisman, W.A., "Relation of the equilibrium contact angle to liquid and solid constitution", Advances in Chem, Ser. pp. 1-51, 1964.

Baier, R.E., Shiafrin, E.G., Zisman, W.A., "Adhesion: Mechanisms that assist or impede it", Science, vol. 162: pp. 1360-1368. 1968.

Fowkes, F.M., "Contact angle, wettability and adhesion", Advances in Chemistry, vol. 43. 1963.

Wu, Souheng. "Surface Tension and Polarity of Solid Polymers". Polymer Interface and Adhesion. Chapter 5. Marcel Dekker, Inc., pp. 169-212, 1982.

Adamson, Arthur W., "Physical Chemistry of Surfaces". 3rd edition. John Wiley & Sons. 1976.

* cited by examiner

IMPLANTABLE OR INSERTABLE MEDICAL ARTICLES HAVING COVALENTLY MODIFIED, BIOCOMPATIBLE SURFACES

TECHNICAL FIELD

This invention relates to medical articles having biocompatible surfaces.

BACKGROUND

A wide variety of medical devices are known, which are adapted for implantation or insertion into the human body. Examples include catheters, cannulae, metal wire ligatures, stents, balloons, filters, scaffolding devices, coils, valves, grafts, plates, and other prosthesis which are adapted for implantation or insertion into various bodily locations, including the heart, coronary vasculature, peripheral vasculature, lungs, trachea, esophagus, intestines, stomach, brain, liver, kidney, bladder, urethra, ureters, eye, pancreas, ovary, and prostate.

In many instances, such medical devices are equipped for the delivery of therapeutic agents. For example, an implantable or insertable medical device, such as a stent or a catheter, may be provided with a polymer matrix that contains a therapeutic agent. Once the medical device is placed at a desired location within a patient, the therapeutic agent is released from the polymer matrix and into the patient, thereby achieving a desired therapeutic outcome.

Regardless of whether or not the implantable or insertable medical device is adapted for release of a therapeutic agent, the material disposed at surface regions of the medical device that come into contact with the body must be reasonably biocompatible for the intended use of the device. The present invention is directed to increasing the biocompatibility of such surface regions.

SUMMARY OF THE INVENTION

In accordance with an aspect of the present invention, an implantable or insertable medical device is provided, which comprises a surface region that is modified by covalently coupling a molecular species (or a combination of molecular species) to the same. The molecular species are selected such that the resulting modified surface region has critical surface energy between 20 and 30 dynes/cm.

An advantage of the present invention is that novel medical devices are provided, which have a critical surface energy value that has been shown to display enhanced biocompatibility, including enhanced thromboresistance, relative to other surfaces.

Another advantage of the present invention is that existing medical devices can be modified to provide them with biocompatible surfaces.

Yet another advantage of the present invention is that modified surface regions are provided which are robust (e.g., they hydrolytically stable) due to the fact that the surface-energy-altering molecular species are directly grafted to the surface regions via covalent bonds.

These and other embodiments and advantages of the present invention will become immediately apparent to those of ordinary skill in the art upon review of the Detailed Description and Claims to follow.

DETAILED DESCRIPTION

In accordance with an aspect of the present invention, an implantable or insertable medical device is provided, which comprises a surface region that is modified by covalently coupling a molecular species (or a combination of molecular species) to the same. The molecular species are selected such that the resulting modified surface region has a critical surface energy between 20 and 30 dynes/cm.

Surfaces having a critical surface energy between 20-30 dynes/cm have been shown in work by Dr. Robert Baier and others to provide enhanced biocompatibility, including enhanced thromboresistance. See, e.g., Baier R E, Meenaghan M A, Hartman L C, Wirth J E, Flynn H E, Meyer A E, Natiella J R, Carter J M, "Implant Surface Characteristics and Tissue Interaction", *J Oral Implantol,* 1988, 13(4), 594-606; Robert Baier, Joseph Natiella, Anne Meyer, John Carter, "Importance of Implant Surface Preparation for Biomaterials with Different Intrinsic Properties in Tissue Integration in Oral and Maxillofacial Reconstruction"; *Current Clinical Practice Series* #29, 1986; Robert Baier, Joseph Natiella, Anne Meyer, John Carter, Fornalik, M. S., Turnbull, T., "Surface Phenomena in In Vivo Environments. Applications of Materials Sciences to the Practice of Implant Orthopedic Surgery", NATO Advanced Study Institute, Costa Del Sol, Spain, 1984; Baier R E, Meyer A E, Natiella J R, Natiella R R, Carter J M, "Surface properties determine bioadhesive outcomes: methods and results", *J Biomed Mater Res,* 1984, 18(4), 327-355; Joseph Natiella, Robert Baier, John Carter, Anne Meyer, Meenaghan, M. A., Flynn, H. E., "Differences in Host Tissue Reactions to Surface-Modified Dental Implants", 185th ACS National Meeting, American Chemical Society, 1983.

In this regard, methods are known for measuring critical surface energy of the surface regions and include a measured critical surface energy between 20 and 30 dynes/cm using any of the following: the use of contact angle methods to produce a Zisman Plot for calculating critical surface tensions as described in Zisman, W. A., "Relation of the equilibrium contact angle to liquid and solid constitution," *Adv. Chem. Ser.* 43, 1964, pp. 1-51; Baier R. E., Shiafrin E. G., Zisman, W. A., "Adhesion: Mechanisms that assist or impede it," *Science,* 162: 1360-1368, 1968; Fowkes, F. M., "Contact angle, wettability and adhesion," Washington D.C., *Advances in Chemistry,* vol. 43, 1964, p. 1, Souheng Wu, *Polymer Interface and Adhesion,* Marcel Dekker, 1982, Chapter 5, pp. 169-212.

A variety of molecular species are available for covalent coupling to medical device surface regions in accordance with the present invention. The covalently coupled molecular species are selected such that the resulting modified surface region has a critical surface energy between 20 and 30 dynes/cm. Covalently coupled molecular species can be selected from the molecular species described below, among others.

For example, covalently attached molecular species can be selected from molecular species comprising one or more methyl groups, for instance, methyl-containing alkyl groups containing 1-100 carbon atoms, more typically 1-25 carbon atoms, even more typically 1-10 carbon atoms, yet more typically 1-5 carbon atoms, which include the following: (i) —$CH_3$; (ii) —$(CH_2)_p$—CH(—$CH_3)_2$, wherein p is an integer typically ranging from 0 to 10, more typically 0 to 5; and (iii) —$(CH_2)_p$—C(—$CH_3)_3$, wherein p is an integer typically ranging from 0 to 10, more typically 0 to 5.

A variety of chemistries are available for linking such alkyl groups to the substrate. In accordance with one beneficial group of techniques discussed further below, alkyl groups are linked to surface via the following linkage: —O—Y(—O—R)$_n$, where R is an alkyl group such as those set forth in the prior paragraph, where Y is an atom selected from Si, Ti, Sn, Ge, V, Mo, W, B and P, and where n is an integer of 1 or more, up to the valence of the Y atom minus 1. For instance, where Y is Si, the valence is 4, so n can be 1, 2 or 3, beneficially 3, as this gives the highest density of covalently attached molecular species.

Additional covalently attached molecular species are selected from the following: (a) molecular species that comprises poly(vinyl fluoride), (b) molecular species that comprise poly(vinylidene fluoride), (c) molecular species that comprise polytrifluoroethylene, (d) molecular species that comprise poly(tetraflouroethylene/chlorinated tetraflouroethylene) copolymer (e.g., in a 60/40 and in a 80/20 molar ratio), (e) molecular species that comprise poly(ethylene/tetraflouroethylene) copolymer (e.g., in a 50/50 molar ratio), (f) molecular species that comprise poly(n-hexyl methacrylate), (g) molecular species that comprise poly(octyl methacrylate), (h) molecular species that comprise poly(lauryl methacrylate), (i) molecular species that comprise poly(stearyl methacrylate), (j) molecular species that comprise poly(dimethylsiloxane), (k) molecular species that comprise poly(isobutylene) and (l) molecular species that comprise hexatriacontane.

Other covalently attached molecular species are selected from covalently attached toluidine red and covalently attached octadecylamine radicals.

For further information on critical surface energies of many of the above and various other materials, see, e.g., Arthur W. Adamson, *Physical Chemistry of Surfaces*, 3$^{rd}$ ed., John Wiley, 1976, pg. 355; and Souheng Wu, *Polymer Interface and Adhesion*, Marcel Dekker, 1982, pp. 184-188.

It is further noted that a combination of molecular species can be covalently attached to the surface region to produce the desired surface energy. For example, in one embodiment, a relatively high critical surface energy polymer, e.g. polyethylene oxide, is grafted to the surface concurrently with a relatively low critical surface energy polymer, e.g., polytetraflouroethylene, in order to produce the desired surface energy.

It is also beneficial in some embodiments to use a combination of molecular species to optimize surface properties, e.g., to reduce surface tack, while at the same time maintaining the desired surface energy. For example, while a butyl acrylate surface may have the desired critical surface energy due to a high concentration of methyl groups, such a surface may also exhibit high tack, which is undesirable in some applications. Co-grafting this species with a fluorine-containing compound of appropriate surface energy, however, is expected to reduce the surface tack.

Surface regions that are covalently modified in accordance with the present invention include ceramic surface regions, metallic surface regions, polymeric surface regions, and combinations of the same.

Examples of ceramic materials for surface modification can be selected, for example, from those comprising one or more of the following: metal oxides, including aluminum oxides and transition metal oxides (e.g., oxides of titanium, zirconium, hafnium, tantalum, molybdenum, tungsten, rhenium, and iridium); silicon-based ceramics, such as those containing silicon nitrides, silicon carbides and silicon oxides (sometimes referred to as glass ceramics); calcium phosphate ceramics (e.g., hydroxyapatite); and carbon-based ceramic-like materials such as carbon nitrides.

Examples of metallic materials for surface modification (which may or may not have a natural or man-made native oxide surface) can be selected, for example, from those comprising one or more of the following: metal alloys such as cobalt-chromium alloys, nickel-titanium alloys (e.g., nitinol), cobalt-chromium-iron alloys (e.g., elgiloy alloys), nickel-chromium alloys (e.g., inconel alloys), and iron-chromium alloys (e.g., stainless steels, which contain at least 50% iron and at least 11.5% chromium), and noble metals such as silver, gold, platinum, palladium, iridium, osmium, rhodium, titanium, tungsten, and ruthenium.

Examples of polymeric materials for surface modification can be selected, for example, from those comprising one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Such polymers may be provided in a variety of configurations, including cyclic, linear and branched configurations. Branched configurations include star-shaped configurations (e.g., configurations in which three or more chains emanate from a single branch point), comb configurations (e.g., graft polymers having a main chain and a plurality of branching side chains), and dendritic configurations (e.g., arborescent and hyperbranched polymers). The polymers can be formed from a single monomer (i.e., they can be homopolymers), or they can be formed from multiple monomers (i.e., they can be copolymers) that can be distributed, for example, randomly, in an orderly fashion (e.g., in an alternating fashion), or in blocks.

In some embodiments, the surface region for modification corresponds to a coating that extends over all or a portion of a medical device substrate (e.g., where a metal substrate, such as a stent, is coated with a polymeric layer, whose surface is in turn modified in accordance with the present invention). In other embodiments, the surface region for modification corresponds to a component of the medical device (e.g., where the surface of a polymeric balloon of a balloon catheter is modified in accordance with the present invention). In other embodiments, the surface region for modification corresponds to an entire medical device surface (e.g., where the surface of an all-metallic stent is modified in accordance with the present invention).

In some embodiments, the entire surface of the medical device, medical device component, medical device coating or other medical device region is modified. In others, only a portion of the surface is surface modified. For example, a medical device surface region can be modified in a preselected pattern by selectively processing only selected portions of the surface region (e.g., by masking portions of the surface) or by creating a surface of two (or more) material compositions in which one composition is receptive to covalent coupling and the other composition is not.

In some embodiments, the implantable or insertable medical device is further provided with a therapeutic agent. For example, in some instances, a therapeutic agent is provided within a polymeric matrix that is surface modified in accordance with present invention. In these embodiments, in addition to providing enhanced biocompatibility, the surface modification also regulates the release profile of the medical device.

Where utilized, the therapeutic agent is introduced into the medical device before or after the covalent modification of the surface region(s) of the medical device.

For example, in certain embodiments, a fluid containing a dissolved or dispersed therapeutic agent is contacted with a surface region subsequent to its modification in accordance with the present invention. Fluids include water, organic solvents, and mixtures of the same. Examples of useful techniques for establishing such contact include spray coating, coating with an applicator (e.g., a roller or brush), spin-coating, dip-coating, web coating, coating via mechanical suspension, including air suspension coating (e.g., fluidized coating), transferring coating, inkjet/solenoid type coating techniques, electrostatic techniques, and so forth.

Therapeutic agents are loaded in accordance with the present invention for any number of purposes, for example, to effect in vivo release (which may be, for example, immediate or sustained) of the biologically active agents, to affect tissue adhesion vis-a-vis the medical device, to influence thromboresistance, to influence antihyperplastic behavior, to enhance recellularizaton, and to promote tissue neogenesis, among many other purposes.

"Biologically active agents," "drugs," "therapeutic agents," "pharmaceutically active agents," "pharmaceutically active materials," and other related terms may be used interchangeably herein and include genetic biologically active agents, non-genetic biologically active agents and cells. Biologically active agents may be used singly or in combination.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines, and (r) hormones.

Preferred non-genetic biologically active agents include paclitaxel, sirolimus, everolimus, tacrolimus, halofuginone agents, including halofuginone hydrobromide, dexamethasone, estradiol, ABT-578 (Abbott Laboratories), trapidil, liprostin, Actinomcin D, Resten-NG, Ap-17, abciximab, clopidogrel and Ridogrel.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermnal growth factor, transforming growth factor α and β, platelet-derived endothelial growth factor, platelet-derived growth factor, tumor necrosis factor a, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP 1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous biologically active agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including a-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartan, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional biologically active agents, not necessarily exclusive of those listed above, are also disclosed in U.S. Pat. No. 5,733,925 assigned to NeoRx Corporation, the entire disclosure of which is incorporated by reference.

Where the medical devices of the present invention contain therapeutic agents, a wide range of drug loading levels can be employed, with the amount of loading being readily determined by those of ordinary skill in the art depending, for example, upon the condition to be treated, the nature of the biologically active agent, the means by which the biologically active agent is administered to the intended subject, and so forth.

Medical devices for use in conjunction with the present invention include those that are implanted or inserted into the body and can be selected, for example, from the following: orthopedic prosthesis such as bone grafts, bone plates, joint prosthesis, central venous catheters, vascular access ports, cannulae, metal wire ligatures, stents (including coronary vascular stents, cerebral, urethral, ureteral, biliary, tracheal, gastrointestinal and esophageal stents), stent grafts (e.g., endovascular stent-grafts), vascular grafts, catheters (for example, renal or vascular catheters such as balloon catheters), guide wires, balloons, filters (e.g., vena cava filters), tissue scaffolding devices, tissue bulking devices, embolization devices including cerebral aneurysm filler coils (e.g., Guglilmi detachable coils, coated metal coils and various other neuroradiological aneurysm coils), heart valves, left ventricular assist hearts and pumps, artificial heart housings, and total artificial hearts.

As noted above, the medical devices of the present invention may be used for essentially any therapeutic purpose, including systemic treatment or localized treatment of any mammalian tissue or organ. Examples include tumors; organs including but not limited to the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone. As used herein, "treatment" refers to the prevention of a disease or condition, the reduction or elimination of symptoms associated with a disease or condition, or the substantial or complete elimination a disease or condition. Preferred subjects (also referred to as "patients") are vertebrate subjects, more preferably mammalian subjects and more preferably human subjects.

Other aspects of the present invention are directed to methods by which a molecular species is covalently coupled to a surface region of an implantable or insertable medical device in order to create a modified surface region that has a critical surface energy between 20 and 30 dynes/cm. Examples of reactions that are used for this purpose are condensation reactions, addition regions, and substitution reactions.

For example, in some embodiments of the present invention, a molecular species is covalently coupled to the surface region of a medical device by a method that comprises: (a) halogenating a surface region of medical device (which surface region can correspond to all or a portion of the medical device as discussed above); and (c) reacting the halogenated surface region with a reactive molecule that is covalently reactive with the chlorinated surface region.

In accordance with certain beneficial embodiments of the invention, the surface region is halogenated by exposing the exposing the surface region to a reactive chloride, for example, a reactive chloride selected from the following: SiCl$_4$ (silicon tetrachloride), TiCl$_4$ (titanium tetrachloride), GeCl$_4$ (germanium tetrachloride), SnCl$_4$ (tin tetrachloride), VCl$_4$ (vanadium tetrachloride), MoCl$_5$ (molybdenum pentachloride), WCl$_6$ (tungsten hexachloride), BCl$_3$ (boron trichloride), and PCl$_5$ (phosphorus pentachloride).

According to a specific embodiment, a surface region (e.g., a metal or a ceramic surface region with available hydroxide groups) is reacted with silicon teatrachloride as a halogenating agent (in this instance, a chlorosilanization agent). This reaction scheme can be represented, for example, as follows:

M-OH+SiCl$_4$M-O—SiCl$_3$+HCl, where M corresponds to the metal or ceramic surface. Note that impurities such as water are typically kept to a minimum. For example, the presence of water can lead to undesirable hydrolysis reactions.

Once they are produced on the surface, the chorosilane groups are then exposed to a molecule that is reactive with the same, thereby forming a covalently coupled molecular species.

For example, in certain beneficial embodiments, the reactive molecule is a compound of the formula Z—R, where R is an alkyl group such as those described above, and where Z is a hydroxyl group. Examples include HO—CH$_3$ and HO—C—(CH$_3$)$_3$, among many others. In the specific case where the reactive molecule is t-butanol, the above reaction scheme is continued as follows:

M-O—SiCl$_3$+HOC(CH$_3$)$_3$M-O—Si[—O—C(CH$_3$)$_3$]$_3$.

As in the prior step, impurities such as water are preferably kept to a minimum. Note that—C(CH$_3$)$_3$ groups are now covalently bonded to the surface, thereby providing a hydrolytically stable monolayer of tert-butyl groups at the device surface.

The above scheme can be conducted on a wide variety of surfaces, including various metallic and ceramic surfaces, so long as surface hydroxyl groups are available for reaction. This scheme can also be conducted on various metals which form native oxide layers. In this regard, controlled native oxide layers can be built up on most metals used today in medical devices. This technology is well known in the art.

The above reaction scheme can also be conducted on surface regions which have been pretreated to establish hydroxyl groups thereon. For example, in some embodiments, a surface region, for example, a polymeric surface region, is pretreated by subjecting it to a glow discharge step. See, e.g., U.S. Pat. No. 5,849,368 entitled "Process for hydrophilicization of hydrophobic polymers" to Hostettler et al., the disclosure of which is hereby incorporated by reference, which describes treatment with an oxygen-containing plasma gas to affix various groups, including hydroxyl groups to a polymeric substrate surface. See also, M-S Sheu, D M Hudson and I-H Loh, "Biomaterials modification using plasma gas discharge processes," Encyclopedic Handbook of Biomaterials, Donal Wise et al., Eds., Marcel Dekker, Inc., NY, pp. 865-894, 1995. The resulting surface region, which is hydroxylated during the glow discharge step, is then available for reaction in accordance with the above scheme.

In other embodiments, the surface region is etched with an acid (e.g., HF, HCl, nitric, etc.) to remove any surface oxide, prior to chlorinating the surface. For example, where the surface region contains silicon atoms, the substrate can be etched with acid, followed by halogenation, for example, using a solution of PCl$_5$ in organic solvent (e.g., chlorobenzene) with a free radical initiator (e.g., benzoyl peroxide) added as a radical initiator, along the lines described in U.S. Patent Application No. 2002/0171082, the disclosure of which is incorporated by reference. Subsequently, the chlorinated surface is subjected to an alkyl-containing reagent, e.g., those of the type R-M and R-M-X, where R is an alkyl group such as those previously discussed, M is a metal atom, and X is a halogen atom. Specific examples include Grignard reagents (i.e., where M is magnesium and X is chlorine, bromine or iodine) and alkyl-lithium reagents (i.e., where M is lithium).

In still other embodiments, for example, where the surface region contains silicon atoms, the surface is etched under conditions conducive to hydrogenation (i.e., hydride formation), for example, by etching with ammonium fluoride along the lines described in U.S. Patent Application No. 2002/0139975, the disclosure of which is incorporated by reference. Subsequently, the hydride surface is exposed to an alkylating reagent such as those described in the prior paragraph.

In yet other embodiments of the invention, vinyl species are attached to the medical device surface. One way of attaching vinyl species to a surface region is by free radical grafting. As a specific example, a polyolefin surface region (e.g., an atactic polypropylene surface region or a low density polyethylene surface region) is pre-treated with ozone (e.g., with 38 mg ozone/liter at 40° C. for one hour) to produce hydroxyperoxide groups on the polymer surface. This pretreated surface is then heated (e.g., to 120° C.) in the presence of a vinyl species of interest (e.g., for 30 minutes) to attach the vinyl species to the surface. This reaction is described in E. M. Fettes, "Chemical Reactions of Polymers", Interscience Publishers, 1964, pp. 1036-1040. For instance, by attaching a vinyl species of the formula $CH_2=C(R_1)COOR$ using this technique (wherein $R_1$ is selected from —H and —$CH_3$ and wherein R is an alkyl group containing one or more methyl groups, e.g., t-butyl acrylate or t-butyl methacrylate), a surface layer of —$CH_2C(R_1)COOR$— groups is provided.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising a modified polymeric surface region, said polymeric surface region being modified by covalently coupling a molecular species or a combination of molecular species to said polymeric surface region such that a modified polymeric surface region having a critical surface energy between 20 and 30 dynes/cm is created, wherein said molecular species comprises a —O—Y(—O—R)$_n$ group, where Y is an atom selected from Si, Ti, Sn, Ge, V, Mo, W, B and P, where n is an integer ranging from 1 up to the valence of the Y atom minus 1 and where R is an alkyl group having from 1 to 100 carbon atoms and comprising one or more methyl groups.

2. The implantable or insertable medical device of claim 1, further comprising a therapeutic agent dispersed within said polymeric surface region.

3. The implantable or insertable medical device of claim 1, wherein said polymeric surface region is a polymeric coating.

4. The implantable or insertable medical device of claim 3, further comprising a therapeutic agent dispersed within said polymeric coating.

5. The implantable or insertable medical device of claim 1, wherein n is one less than the valence of the atom Y.

6. The implantable or insertable medical device of claim 5, wherein Y is Si and n=3.

7. The implantable or insertable medical device of claim 5, wherein Y is Ti and n=3.

8. The implantable or insertable medical device of claim 1, wherein a plurality of molecular species of the formula —$CH_n(CH_3)_{3-n}$ where n is 0, 1 or 2, are covalently coupled to said surface region.

9. The implantable or insertable medical device of claim 1, wherein said modification of said polymeric surface region improves the thromboresistance of said medical device polymeric surface region relative to said polymeric surface region in the absence of said modification.

10. The implantable or insertable medical device of claim 1, wherein said medical device is selected from cardiovascular stents, cardiovascular catheters, prosthetic heart valves, artificial heart housings, vascular grafts, endovascular stent-grafts, and neuroradiological aneurysm coils.

11. The implantable or insertable medical device of claim 1, wherein said molecular species is covalently coupled to said surface region by a method comprising: (a) chlorinating said polymeric surface region of said medical device thereby forming a chlorinated polymeric surface region; and (b) reacting said chlorinated polymeric surface region with a reactive molecule.

12. The implantable or insertable medical device of claim 11, wherein said chlorinated polymeric surface region is formed by exposing a hydroxylated polymeric surface region to a reactive chloride selected from $SiCl_4$, $TiCl_4$, $SnCl_4$, $GeCl_4$, $VCl_4$, $MoCl_5$, $WCl_6$, $BCl_3$, and $PCl_5$.

13. The implantable or insertable medical device of claim 12, wherein said reactive compound is of the formula Z—R, where R is an alkyl group comprising one or more methyl groups and having from 1 to 10 carbon atoms, and wherein Z is hydroxyl.

14. The implantable or insertable medical device of claim 13, wherein said reactive compound is $HOC(CH_3)_3$.

15. The implantable or insertable medical device of claim 11, wherein said surface is hydroxylated by glow discharge prior to said chlorinating step.

* * * * *

UNITED STATES PATENT AND TRADEMARK OFFICE
CERTIFICATE OF CORRECTION

| | | |
|---|---|---|
| PATENT NO. | : 7,767,220 B2 | |
| APPLICATION NO. | : 10/830772 | |
| DATED | : August 3, 2010 | |
| INVENTOR(S) | : Helmus et al. | |

It is certified that error appears in the above-identified patent and that said Letters Patent is hereby corrected as shown below:

Col. 6, line 61, after "helial growth factor,", change "epidermnal" to -- epidermal--.

Col. 6, line 63, after "necrosis factor", change "a" to -- $\alpha$ --.

Col. 7, line 52, after "including", change "a" to -- $\alpha$ --.

Signed and Sealed this
Eighteenth Day of January, 2011

David J. Kappos
*Director of the United States Patent and Trademark Office*